United States Patent [19]

Su et al.

[11] 3,992,215

[45] Nov. 16, 1976

[54] PHARMACEUTICAL SUSPENSION FOR OPAQING EMPTY GELATIN CAPSULES

[75] Inventors: Kenneth S. E. Su; Ronald R. Snyder; R. Ray Scott, all of Indianapolis, Ind.

[73] Assignee: Eli Lilly and Company, Indianapolis, Ind.

[22] Filed: May 8, 1975

[21] Appl. No.: 575,563

[52] U.S. Cl. .................. 106/287 SB; 106/137; 106/300; 106/308 F; 260/29.2 M; 427/37
[51] Int. Cl.² .................. A61K 47/00; C09C 1/36; C09K 3/00
[58] Field of Search .............. 106/287 SB, 312, 300, 106/137, 135, 136, 287; 424/31–37, 360; 260/29.2 M; 428/405; 427/3; 252/316

[56] References Cited
UNITED STATES PATENTS

| | | | |
|---|---|---|---|
| 2,195,926 | 4/1940 | Hoskins | 106/136 |
| 2,776,220 | 1/1957 | Reed | 106/135 |
| 3,520,971 | 7/1970 | Benford | 424/360 |
| 3,653,934 | 4/1972 | Rolle | 424/360 |
| 3,729,423 | 4/1973 | Hirota | 252/316 |

OTHER PUBLICATIONS

Chem Abst 75:43, 119 m 1970.

*Primary Examiner*—Theodore Morris
*Attorney, Agent, or Firm*—Ralph W. Ernsberger; Everet F. Smith

[57] ABSTRACT

A pharmaceutical suspension of titanium dioxide for use in admixing with gelatin solutions for the manufacture of empty opaque gelatin capsules is provided which comprises: titanium dioxide, glycerin, sodium lauryl sulfate, simethicone, sodium citrate and water. A process is also provided which entails the requirement for adding the sodium citrate as the final ingredient in the suspension.

6 Claims, No Drawings

PHARMACEUTICAL SUSPENSION FOR OPAQING EMPTY GELATIN CAPSULES

BACKGROUND OF THE INVENTION

1. Field of the Invention

This invention relates to a pharmaceutical suspension. More particularly, the instant invention is concerned with a suspension of titanium dioxide for use in admixing with gelatin solutions from which opaque empty gelatin capsules can be manufactured which are suitable as containers for unit doses of pharmaceutically active agents.

2. Prior Art

Almost all of the billions of empty gelatin capsules used each year in the world are manufactured by dipping highly polished, but lubricated, forming pins into a warm viscous gelatin solution. The forming pin is slowly withdrawn from the solution with a thin film of gelatin adhering thereto. The gelatin film is dried on the forming pin until the moisture content of the film is somewhere in the neighborhood of 13–16 percent, preferably about 14–15 percent. A special stripping tool is used to remove the gelatin film from the forming pin and the edges of the open end of the gelatin are trimmed to provide one of the two pieces of an empty gelatin capsule. Separate forming pins of different diameters are used to form each of the two pieces of an empty capsule so that, when properly trimmed, the two pieces will telescope together to make a package which can be filled with various physiologically active agents to provide a pharmaceutical unit dosage form.

Gelatin is a material which has been used since the late nineteenth century for making capsules for use in holding unit dosage forms of various active agents.

A simple solution (actually a colloidal solution) of gelatin can be used to make capsules in the manner described briefly above. It is preferred, however, to include preservatives in the gelatin solution because in such solution gelatin is a highly desirable substrate for microbial growth. And when the organisms are gas formers, little bubbles appear in the solution which are not easy to remove.

Early capsules were made without coloring and, if the gelatin was of good quality, such capsules would be essentially transparent. Later on various approved soluble dyes were added to the gelatin solution to make capsules of various colors. Even so, such capsules, colored or plain, came to be known as clear capsules.

As the demand for empty gelatin capsules increased, a need arose for a wider range of colors and hues for use in identifying different medicaments. A group of opaque capsules were developed to meet this need, and titanium dioxide was adopted as the opaquing agent because of its lack of toxicity and high opaquing properties.

Opaquing grade titanium dioxide must be finely divided particles, preferably in the micron range. Generally, particles this small are difficult to wet, and titanium dioxide is no exception. It was soon found that it was impractical to mix finely-divided titanium dioxide powder directly into a viscous gelatin solution. Consequently, paste formulations of titanium dioxide were developed which could be mixed into the viscous gelatin solution with only moderate difficulty. However, these titanium pastes had to be prepared very nearly simultaneously with the preparation of the gelatin solution as the pastes tended to coalesce and harden within a short time.

Then it was discovered that the addition of glycerin to the paste formulation would substantially retard the hardening and make it possible to prepare such a paste many days ahead of its use.

Sometime later a suspension of titanium dioxide was developed which was suitable for admixing with a solution of gelatin for the manufacture of opaque gelatin capsules. And, for many years this suspension proved satisfactory for its purpose. It consisted essentially of titanium dioxide powder, glycerin, water, and the preservatives methylparaben, propylparaben. Later chloroform and alcohol S.D.A. No. 20 were added.

Then a few months ago it became impossible to obtain adequate amounts of the grade of titanium dioxide which had been used for years in preparing the suspension. A new supplier of titanium dioxide was found and a different grade of titanium dioxide was substituted for that which had been used in the past. With the new grade of titanium dioxide it was no longer possible to prepare a suitable suspension having a viscosity within the range required for effective additions to gelatin solutions. And, when a mixture of the titanium dioxide and the gelatin solution was accomplished, the capsules produced therefrom were grainy and reflected light unevenly. It was learned that, even though an analysis of the particle size of the two grades indicated a similar range of sizes, an average of about 1 micron, one grade, the longused quality, was specified as an oil dispersible material, whereas the newer material was categorized as a water dispersible grade. This classification was supported by the fact that a 25 percent aqueous suspension of the so-called oil dispersible grade had a viscosity of between 1,400 and 2,200 centipoises at 25° C., and a similarly prepared aqueous suspension of the water dispersible grade had a viscosity of about 3 centipoises at 25° C. It was also found that the water dispersible grade of titanium dioxide had a zeta potential of about −35 millivolts whereas the oil dispersible material had exhibited a zeta potential of −17 to −27 millivolts.

Accordingly, it is an object of this invention to provide a pharmaceutical suspension of titanium dioxide of either oil or water dispersible grades that can be admixed with gelatin solutions for manufacturing empty opaque capsules of consistent quality.

Another object of this invention is to provide a process for preparing a pharmaceutical suspension of titanium dioxide utilizing either oil or water dispersible titanium dioxide, said suspension being for use in admixing with gelatin solutions for manufacturing empty opaque capsules of consistent quality.

Still another object of this invention is to provide a pharmaceutical suspension of titanium dioxide of whatever source or grade that resists caking and settling of the dispersed phase and which, after dead storage for a year or more, can be readily re-suspended by simple shaking or stirring.

SUMMARY

It has now been discovered that a satisfactory pharmaceutical suspension of titanium dioxide for use in admixing with gelatin solutions for the manufacture of empty opaque capsules utilizing titanium dioxide from any source comprises:

a. commingling sodium lauryl sulfate with purified water;

b. adding thereto simethicone;
c. blending finely-divided titanium dioxide with the preparation from b);
d. adding glycerin to the preparation from c); and
e. commingling sodium citrate with the preparation from d).

A process for this preparation is also provided which, among other things, requires that the sodium citrate is the final ingredient added to the suspension. The resulting suspension, when the titanium dioxide content is about 32.5 percent (W/V) exhibits a viscosity of about 800 centipoises when water dispersible titanium is employed, and about 1,000 centipoises when oil dispersible titanium dioxide is used. Both suspensions are suitable for use in manufacturing empty opaque gelatin capsules.

DESCRIPTION OF THE PREFERRED EMBODIMENTS

One aspect of this invention relates to a useful pharmaceutical suspension for use in preparing opaque gelatin capsules. An appropriate quantity of this suspension is admixed with a solution of gelatin before the capsule is formed from such an admixture. This novel suspension is comprised of:

a) titanium dioxide; b) glycerin; c) sodium lauryl sulfate; d) simethicone; e) sodium citrate, and f) water.

The titanium dioxide, the actual opaquing agent, is a white odorless, tasteless powder which for the instant use has a particle size wherein not less than 100 percent must pass a No. 200 U.S. standard mesh screen. Titanium dioxide is official in the United States Pharmacopeia (U.S.P.) XIX, page 509. There are two grades of titanium dioxide recognized in the trade; one is an oil dispersible grade and the other is known as a water dispersible grade. For the present use, the preferred grade is the oil dispersible material, although either grade can be used as long as the U.S.P. XIX specifications are met.

Glycerin is a clear, colorless, syrupy liquid, having a sweet taste. It is official in U.S.P. XIX, the monograph appearing on pages 222–3. In the instant invention it is employed both as a viscosity and specific gravity adjusting agent and a humectant.

Sodium lauryl sulfate is a white or light yellow powder having a characteristic odor. It is official in U.S.P. XIX, pages 572–3. It is used in the useful suspension of this invention as a surfactant.

The simethicone in the suspension is employed as an antifoam agent. It is added to the suspension vehicle as an emulsion. Simethicone is official in The National Formulary (NF) XIV, p. 648. One brand of simethicone is Dow Corning's Medical Antifoam A Compound. Chemically, simethicone is a dimethylpolysiloxane and is a mixture of polymers of varying molecular weights. It is a translucent, gray, viscous fluid. In this invention it is preferred to use an emulsion of the simethicone in preparing the useful suspension of titanium dioxide. A 30 percent emulsion of simethicone is available from Dow Corning, Midland, Mich. under the designation of Medical Antifoam AF Emulsion. In addition to the 30 percent simethicone, the Antifoam AF Emulsion also contains 14 percent stearate emulsifiers and 0.075 percent sorbic acid, neither of the latter two ingredients being part of this invention, but they become part of the composition of the suspension when the AF emulsion is used as the source of the simethicone.

Sodium citrate is a colorless or white crystalline material. It is official in U.S.P. XIX, page 458. Its use in the novel suspension of this invention aids in establishing a suitable specific gravity and viscosity in the suspension.

Purified water is official in U.S.P. XIX, the monograph appearing on pages 540–1.

The novel suspension of the instant invention can contain from about 10 to about 40 percent (W/V) of titanium dioxide; from about 5 to about 20 percent (V/V) of glycerin; from about 0.05 to about 0.15 percent (W/V) of sodium lauryl sulfate; from about 0.015 to about 0.03 percent (W/V) of simethicone; from about 0.5 to about 5.0 percent (W/V) of sodium citrate; and purified water q.s. to 100 parts by volume.

A particularly preferred suspension is comprised of about 32.5 percent (W/V) of titanium dioxide; about 11.5 percent (V/V) of glycerin; about 0.08 percent (W/V) of sodium lauryl sulfate; about 0.024 percent (W/V) of simethicone; about 3 percent (W/V) of sodium citrate; and purified water q.s. to 100 parts by volume.

The useful suspension of this invention can also include a preservative or preservatives such as the parabens, ethyl alcohol, chloroform, and the like. A preferred combination of preservatives includes methylparaben, propylparaben, chloroform and alcohol S.D.A. No. 20, the latter being ethyl alcohol denatured with chloroform. These agents are combined with the preferred suspension in amounts related to the total composition of about 0.3 percent (W/V) of methylparaben, about 0.035 percent (W/V) of propylparaben, about 0.3 percent (V/V) of chloroform, and about 0.3 percent (V/V) of alcohol S.D.A. No. 20.

In another aspect of the instant invention, the useful pharmaceutical suspension of titanium dioxide can be prepared by:

a. commingling, with agitation, sodium lauryl sulfate and simethicone in an emulsion containing about 30 percent of the silicone with purified water;
b. blending, with agitation, titanium dioxide with the preparation from a);
c. dispersing, with continuous agitation, the titanium dioxide in the preparation from b) and adding glycerin to this preparation either during or after the conclusion of the hydration, and
d. adding to the preparation from c), with agitation, after all of the aforementioned ingredients have been combined, sodium citrate.

In this process it is absolutely essential that the sodium citrate be added after the dispersion of the titanium dioxide in the suspension is complete. Experience showed that if the sodium citrate is added before the addition of oil dispersible grade titanium dioxide, the viscosity becomes inordinately high and completely unsatisfactory. On the other hand, adding the sodium citrate after the dispersion of the oil dispersible grade titanium dioxide adds little, if any, to the viscosity of the suspension.

When sodium citrate is added to a suspension of water dispersible titanium dioxide, the effect of such addition to the viscosity is about the same whether the sodium citrate is added before or after the dispersion of the titanium dioxide. However, the sodium citrate is an essential ingredient in the suspension as it has a dramatic affect on the viscosity, actually increasing the viscosity of a suspension in which water dispersible titanium dioxide is used by $10^2$ to $10^3$ times. In effect, sodium citrate stabilizes the viscosity of the suspension in a range which, combined with the other factors involved, aids in slowing the rate of settling of the suspension. While the inclusion of sodium citrate in the suspension does not bring the viscosities of suspensions made from oil dispersible and water dispersible titanium dioxide, respectively, into identical or closely similar agreement, the differences are generally less than 20 and always less than 30 percent.

This useful process also requires the addition of the surfactant, sodium lauryl sulfate and the antifoam agent, simethicone to purified water before the titanium dioxide is dispersed therein. The surfactant aids in wetting the titanium dioxide in the preparation of the dispersion. The antifoam agent is included in the suspension in order to counteract the foaming effect of the sodium lauryl sulfate on the gelatin solution when the suspension is added thereto. The gelatin solution to which the suspension is added is a thick viscous tenacious solution in which bubbles, once they are formed or incorporated, are extremely difficult to remove. And, gas bubbles in the gelatin are carried along in the film adhering to the forming pin and generally remain in the film after it is dried. Bubbles in the capsules weaken the structure, are unsightly, and tend to destroy the pharmaceutical elegance of the capsule. Consequently, the quantity of surfactant included in the titanium dioxide suspension is kept to a minimum by avoiding the use of excess quantities which do nothing more to reduce the surface tension of the water.

The antifoam agent, simethicone, effectively inhibits the foaming induced by the surfactant. The concern is not about the foaming produced in the suspension per se, but in the gelatin solution to which the suspension is added as an opaquing agent. However, the presence of the antifoam agent in the purified water, along with the surfactant, allows the dispersion of the titanium dioxide to be effected with very vigorous agitation with only a minimum of foaming, thus hastening the dispersion of the titanium dioxide.

When the useful pharmaceutical dispersion of this invention is comprised of only the principal ingredients detailed herein, the preparation of the suspension can proceed with all of the materials and processing steps taking place at room temperature (RT). However, when paraben preservatives are employed, the temperature of the water is raised to 80° C. at the beginning of the process and the parabens are added to the water before any other ingredients are combined therewith. With vigorous agitation, the parabens can be dissolved in the water at about 80° C. in a short time. As soon as the parabens have been dissolved, the surfactant and the antifoam agent can be commingled therewith as the paraben-water preparation is cooling. When the latter two ingredients are thoroughly blended into the vehicle the titanium dioxide powder can be added irrespective of the temperature.

Following the dispersion of the titanium dioxide, the glycerin and sodium citrate can be added to the suspension in that order regardless of the temperature of the suspension. However, if chloroform and alcohol SDA No. 20 are to be added to the suspension as additional preservatives, they are combined with the glycerin in a separate vessel and the combination is added to the suspension only after the temperature of the latter has been lowered to <52° C. This is necessary because of the volatility of the chloroform and the alcohol.

Glycerin in the suspension serves as a specific gravity adjusting agent, bringing the specific gravity nearer to the density of the dispersed phase. Moreover, the glycerin is known to act as a humectant in maintaining the titanium dioxide in the wetted state. Furthermore, glycerin is wholly compatible with gelatin, actually being a recognized plasticizer thereof.

As has been detailed hereinabove, the sodium citrate is added to the suspension only after all of the other ingredients are incorporated therein. The sodium citrate can be added directly to the suspension as the crystalline material. However, it is preferred to dissolve the sodium citrate in part of the purified water, such as in a 30 percent solution, and to add such a solution to the suspension. Thorough blending is faster and the effect of the sodium citrate on the viscosity of the suspension is immediate and complete.

In preparing the useful pharmaceutical suspension of this invention, it is possible to determine the appropriate quantities of each ingredient desired in the final suspension, and to incorporate these into the complete suspension utilizing the novel process described hereinabove. When this process is followed, the quantity of purified water that is to be a part of the complete suspension is determined, and that quantity, less the amount to be used as a solvent for the sodium citrate, is measured out and the ingredients to be incorporated thereinto are added thereto following the manner and sequence outlined above. However, it is preferred to begin the process of preparing this novel suspension by starting with less purified water than will be in the complete suspension, but enough to adequately carry out the various dissolving, dispersing and blending steps, and then to q.s. the suspension to the desired volume after all other operations have been followed.

In the composition of the titanium dioxide suspension and the process for its preparation the various ingredients employed have been specified on a percent weight per volume (W/V), or a percent volume per volume (V/V) basis. In this regard it is understood that consistent units of measurements are equated; for example, 1 g. is equated with 1 ml., et seq. Moreover, in this specification and the claims annexed hereto, parts and percent are synonymous.

The useful process of the instant invention comprises the following steps:
  a. From about 0.05 to about 0.15 parts by weight of sodium lauryl sulfate and from about 0.015 to about 0.03 parts by weight of simethicone contained in a 30 percent emulsion thereof are commingled with about 50 parts by volume of purified water in a suitable vessel with agitation.
  b. From about 10 to about 40 parts by weight of titanium dioxide are dispersed in the preparation from a) with vigorous agitation.
  c. The agitation of the preparation from b) is continued until all of the titanium dioxide is completely wetted and the suspension is smooth.
  d. From about 5 to about 20 parts by volume of glycerin are blended with the preparation from c) with agitation.
  e. From about 1 to about 5 parts by weight of sodium citrate is added, with agitation, to the preparation from d), and
  f. Sufficient water is added to the preparation from e) to q.s. the suspension to 100 parts by volume.

The preferred process of preparing the useful pharmaceutical suspension of the present invention comprises the steps of:
a. About 0.08 parts by weight of sodium lauryl sulfate and about 0.024 parts by weight of simethicone contained in a 30 percent emulsion thereof are commingled with about 50 parts by volume of purified water.
b. About 32.5 parts by weight of titanium dioxide are dispersed in the preparation from a) with vigorous agitation.
c. The agitation of the preparation from b) is continued until all of the titanium dioxide is thoroughly wetted.
d. About 11.5 parts by volume of glycerin is blended with the dispersion from c) with agitation.
e. About 3 parts by weight of sodium citrate contained in an aqueous solution thereof, said solution containing from about 10 to about 60 percent (W/V) of sodium citrate are added to the preparation from d) with agitation, and
f. Sufficient purified water is added to the preparation from e) to q.s. the suspension to 100 parts by volume.

This invention is further illustrated by the following Example I.

Example I

Preparation of 1000 Liters of a Pharmaceutical Suspension Containing 32.5 percent (W/V) of Titanium Dioxide Place in a suitable vessel equipped with means for agitation and heating-

| | | |
|---|---|---|
| Purified Water | 500.0 l. | |
| Heat to about 80° C. | | |
| Add: Methylparaben | 3,021 g. | |
| Add: Propylparaben | 351 g. | |
| Agitate vigorously until solution is complete | | |
| Remove heat and begin cooling | | |
| Add: Antifoam AF Emulsion (30 percent simethicone) | 800 g. | |
| Add: Sodium Lauryl Sulfate | 800 g. | |
| Agitate vigorously | | |
| Add: Titanium Dioxide | 326.3 kg. | |
| Agitate very vigorously. Continue agitation until wetting of titanium dioxide is complete | | |
| Combine in a separate vessel: | | |
| Glycerin | 115 l. | |
| Alcohol SDA No. 20 | 3 l. | |
| Chloroform | 3 l. | |
| Mix well | | |
| Add: Glycerin-alcohol-chloroform combination | | |
| Agitate thoroughly | | |
| Combine: | | |
| Sodium Citrate | 30 kg. | |
| Purified Water | 100 l. | |
| Mix until dissolved | | |
| Add: Sodium Citrate Solution | | |
| Agitate thoroughly | | |
| Add: Purified Water q.s. | 1000 l. | |
| Mix thoroughly | | |
| Package. | | |

The useful pharmaceutical suspension of titanium dioxide of this invention is admixed with gelatin solutions from which empty opaque gelatin capsules are manufactured. Empty gelatin capsules in the popular size o will weigh about 105 mg. and contain from about 1.5 to as much as about 8 percent titanium dioxide. The amount of titanium dioxide present will depend on the particular color and hue desired. Many popular size o capsules contain about 3 percent titanium dioxide. To make these capsules 1 liter of a 32.5 percent titanium dioxide suspension is admixed with about 35 liters of a standard 30 percent gelatin solution from which the capsules are formed. Other concentrations of titanium dioxide in the empty opaque gelatin capsules can be prepared by varying the amount of the titanium dioxide suspension added to the standard gelatin solution.

What is claimed is:
1. A pharmaceutical suspension for opaquing empty gelatin capsules comprised of: a) titanium dioxide; b) glycerin; c) sodium lauryl sulfate; d) fluid dimethyl-polysiloxane; e) sodium citrate, and f) water.
2. The suspension of claim 1 comprising: a) from about 10 to about 40 percent (W/V) of titanium dioxide; b) from about 5 to about 20 percent (V/V) of glycerin; c) from about 0.05 to about 0.15 percent (W/V) of sodium lauryl sulfate; d) from about 0.015 to about 0.03 percent (W/V) of fluid dimethyl-polysiloxane, from about 0.5 to about 5.0 percent (W/V) of sodium citrate, and f) purified water q.s. to 100 parts by volume.
3. The suspension of claim 1 comprising: a) about 32.5 percent (W/V) of titanium dioxide; b) about 11.5 percent (V/V) of glycerin; c) about 0.08 percent (W/V) of sodium lauryl sulfate; d) about 0.024 percent (W/V) of fluid dimethyl-polysiloxane; e) about 3 percent (W/V) of sodium citrate, and f) purified water q.s. to 100 parts by volume.
4. A method of preparing a pharmaceutical suspension of titanium dioxide for use in manufacturing empty opaque gelatin capsules comprising the steps of:
a. commingling, with agitation, sodium lauryl sulfate and fluid dimethyl-polysiloxane contained in a 30 percent emulsion thereof with purified water;
b. dispersing, with vigorous agitation, titanium dioxide into the preparation from a);
c. continuing the agitation of the preparation from b) until all of the titanium dioxide has been thoroughly wetted;
d. adding, with agitation, glycerin to the preparation from c), and
e. adding, with agitation, sodium citrate to the preparation from d).
5. The method of preparing the suspension of claim 4 comprising the steps of:
a. commingling, with agitation, from about 0.05 to about 0.15 parts by weight of sodium lauryl sulfate and from about 0.015 to about 0.03 parts by weight of fluid dimethyl-polysiloxane contained in a 30 percent suspension thereof with about 50 parts by volume of purified water;
b. dispersing, with vigorous agitation, from about 10 to about 40 parts by weight of titanium dioxide in the preparation from a);
c. blending, with agitation, from about 5 to about 20 parts by volume of glycerin with the preparation from b);
d. adding, with agitation, from about 1 to about 5 parts by weight of sodium citrate to the preparation from c); and
e. adding, with agitation, sufficient water to the preparation from d) to q.s. the volume of the suspension to 100 parts by volume.
6. The method of preparing the suspension of claim 4 comprising the steps of:
a. commingling, with agitation, about 0.08 parts by weight of sodium lauryl sulfate and about 0.024 parts by weight of fluid dimethyl-polysiloxane con- tained in a 30 percent emulsion thereof with about 50 parts by volume of purified water;
b. dispersing, with vigorous agitation, about 32.5 parts by weight of titanium dioxide into the preparation from a);
c. continuing the agitation of the preparation from b) until all of the titanium dioxide is thoroughly wetted;
d. blending, with agitation, about 11.5 parts by volume of glycerin in the preparation from c);
e. adding, with agitation, about 3 parts by weight of sodium citrate contained in an aqueous solution, wherein the solute is from about 10 to about 60 percent of the volume, to the preparation from d), and
f. adding, with agitation, sufficient purified water to the preparation from e) to q.s. the suspension to 100 parts by volume.

* * * * *